United States Patent
Gilad et al.

(10) Patent No.: US 8,500,630 B2
(45) Date of Patent: Aug. 6, 2013

(54) IN VIVO DEVICE WITH FLEXIBLE CIRCUIT BOARD AND METHOD FOR ASSEMBLY THEREOF

(75) Inventors: Zvika Gilad, Haifa (IL); Semion Khait, Tiberias (IL)

(73) Assignee: Given Imaging Ltd., Yoqneam (IL)

( * ) Notice: Subject to any disclaimer, the term of this patent is extended or adjusted under 35 U.S.C. 154(b) by 706 days.

(21) Appl. No.: 10/879,054

(22) Filed: Jun. 30, 2004

(65) Prior Publication Data

US 2006/0004257 A1   Jan. 5, 2006

(51) Int. Cl.
 *A61B 1/06* (2006.01)
(52) U.S. Cl.
 USPC .......................................... 600/160
(58) Field of Classification Search
 USPC .................. 600/101, 109, 160, 130
 See application file for complete search history.

(56) References Cited

U.S. PATENT DOCUMENTS

| | | |
|---|---|---|
| 78,134 A | 5/1868 | Robbins |
| 3,509,270 A | 4/1970 | Dube et al. |
| 3,616,532 A | 11/1971 | Beck |
| 3,683,389 A | 8/1972 | Hollis |
| 3,791,377 A | 2/1974 | Norby et al. |
| 3,971,362 A | 7/1976 | Pope et al. |
| 4,087,960 A | 5/1978 | Koichi |
| 4,239,040 A | 12/1980 | Hosoya et al. |
| 4,278,077 A | 7/1981 | Mizumoto |
| 4,439,197 A | 3/1984 | Honda et al. |
| 4,447,677 A | 5/1984 | Miyahra et al. |
| 4,646,724 A | 3/1987 | Sato et al. |
| 4,668,884 A * | 5/1987 | Amao et al. ................ 310/68 R |
| 4,689,621 A | 8/1987 | Kleinberg |
| 4,741,327 A | 5/1988 | Yabe |
| 4,742,183 A | 5/1988 | Soloway et al. |
| 4,742,817 A | 5/1988 | Kawashima et al. |
| 4,803,992 A | 2/1989 | Lemelson |
| 4,819,620 A | 4/1989 | Okutsu |
| 4,844,076 A | 7/1989 | Lesho et al. |
| 4,860,732 A | 8/1989 | Hasegawa et al. |
| 4,936,823 A | 6/1990 | Colvin et al. |
| 4,939,792 A | 7/1990 | Urbish et al. |
| 5,010,412 A | 4/1991 | Garriss |
| 5,025,704 A | 6/1991 | Davis |
| 5,078,134 A | 1/1992 | Heilman et al. |
| 5,187,572 A | 2/1993 | Nakamura et al. |
| 5,217,449 A | 6/1993 | Yuda et al. |

(Continued)

FOREIGN PATENT DOCUMENTS

| | | |
|---|---|---|
| DE | 34 40 177 | 5/1986 |
| EP | 1 104 182 | 5/2001 |

(Continued)

OTHER PUBLICATIONS

U.S. Appl. No. 10/493,751, filed Apr. 27, 2004, Glukhovsky, et.al.

(Continued)

*Primary Examiner* — Philip R Smith
(74) *Attorney, Agent, or Firm* — Pearl Cohen Zedek Latzer, LLP

(57) ABSTRACT

An in vivo imaging device having a flexible circuit board, for example, a one-sheet flexible circuit board. The flexible circuit board may enable folding components attached to the flexible circuit board according to a predefined angle.

20 Claims, 4 Drawing Sheets

(56) References Cited

U.S. PATENT DOCUMENTS

| | | | |
|---|---|---|---|
| 5,250,371 A | 10/1993 | Klienert et al. | |
| 5,267,033 A | 11/1993 | Hoshino | |
| 5,279,607 A | 1/1994 | Schentag et al. | |
| 5,330,427 A | 7/1994 | Weissenburger | |
| 5,368,027 A | 11/1994 | Lubbers et al. | |
| 5,381,784 A | 1/1995 | Adair | |
| 5,395,366 A | 3/1995 | D'Andrea et al. | |
| 5,398,670 A | 3/1995 | Ortiz et al. | |
| 5,398,689 A | 3/1995 | Connor et al. | |
| 5,420,631 A | 5/1995 | Hamasaki | |
| 5,426,263 A | 6/1995 | Potter et al. | |
| 5,448,511 A | 9/1995 | Paurus et al. | |
| 5,454,366 A * | 10/1995 | Ito et al. | 600/109 |
| 5,472,804 A | 12/1995 | Austin et al. | |
| 5,495,114 A | 2/1996 | Adair | |
| 5,508,781 A * | 4/1996 | Imai et al. | 396/529 |
| 5,558,640 A | 9/1996 | Pfeiler et al. | |
| 5,604,531 A | 2/1997 | Iddan et al. | |
| 5,679,216 A | 10/1997 | Takayama et al. | |
| 5,697,384 A | 12/1997 | Miyawaki et al. | |
| 5,725,474 A | 3/1998 | Yasui et al. | |
| 5,734,418 A | 3/1998 | Danna | |
| 5,742,804 A | 4/1998 | Yeh et al. | |
| 5,754,313 A | 5/1998 | Pelchy et al. | |
| 5,807,266 A | 9/1998 | Itonaga et al. | |
| 5,819,736 A | 10/1998 | Avny et al. | |
| 5,833,603 A | 11/1998 | Kovacs et al. | |
| 5,929,901 A | 7/1999 | Adair et al. | |
| 5,984,875 A | 11/1999 | Brune | |
| 5,986,693 A | 11/1999 | Adair et al. | |
| 5,993,378 A | 11/1999 | Lemelson | |
| 6,043,839 A | 3/2000 | Adair et al. | |
| 6,099,482 A | 8/2000 | Brune et al. | |
| 6,121,922 A | 9/2000 | Mohan | |
| 6,149,581 A | 11/2000 | Klingenstein | |
| 6,233,476 B1 | 5/2001 | Strommer et al. | |
| 6,240,312 B1 | 5/2001 | Alfano et al. | |
| 6,276,605 B1 | 8/2001 | Olmstead et al. | |
| 6,313,456 B1 | 11/2001 | Miyashita et al. | |
| 6,324,418 B1 | 11/2001 | Crowley et al. | |
| 6,338,347 B1 | 1/2002 | Chung | |
| 6,371,927 B1 | 4/2002 | Brune et al. | |
| 6,417,885 B1 | 7/2002 | Suzuki et al. | |
| 6,428,469 B1 | 8/2002 | Iddan et al. | |
| 6,632,175 B1 | 10/2003 | Marshall | |
| 6,692,430 B2 | 2/2004 | Adler | |
| 6,709,387 B1 | 3/2004 | Glukhovsky et al. | |
| 6,764,440 B2 | 7/2004 | Iddan et al. | |
| 6,934,573 B1 | 8/2005 | Glukhovsky et al. | |
| 6,939,290 B2 | 9/2005 | Iddan | |
| 6,944,031 B2 * | 9/2005 | Takami | 361/794 |
| 6,944,316 B2 | 9/2005 | Glukhovsky et al. | |
| 6,950,690 B1 | 9/2005 | Meron et al. | |
| 6,958,034 B2 | 10/2005 | Iddan | |
| 7,022,067 B2 | 4/2006 | Glukhovsky et al. | |
| 7,104,952 B2 | 9/2006 | Iddan et al. | |
| 7,118,529 B2 | 10/2006 | Glukhovsky et al. | |
| 2001/0006252 A1 | 7/2001 | Kim et al. | |
| 2001/0017649 A1 | 8/2001 | Yaron | |
| 2001/0035902 A1 | 11/2001 | Iddan et al. | |
| 2001/0051766 A1 | 12/2001 | Gazdzinski | |
| 2002/0103417 A1 | 8/2002 | Gazdzinski | |
| 2002/0146368 A1 | 10/2002 | Meron et al. | |
| 2002/0158976 A1 | 10/2002 | Vni et al. | |
| 2002/0173718 A1 | 11/2002 | Frisch et al. | |
| 2002/0177779 A1 | 11/2002 | Adler et al. | |
| 2002/0198439 A1 | 12/2002 | Mizuno | |
| 2003/0018280 A1 | 1/2003 | Lewkowicz et al. | |
| 2003/0028078 A1 | 2/2003 | Glukhovsky | |
| 2003/0043263 A1 | 3/2003 | Glukhovsky et al. | |
| 2003/0045790 A1 | 3/2003 | Lewkowicz et al. | |
| 2003/0114742 A1 | 6/2003 | Lewkowicz et al. | |
| 2003/0117491 A1 | 6/2003 | Avni et al. | |
| 2003/0167000 A1 | 9/2003 | Mullick et al. | |
| 2003/0171648 A1 | 9/2003 | Yokoi et al. | |
| 2003/0171649 A1 | 9/2003 | Yokoi et al. | |
| 2003/0171652 A1 | 9/2003 | Yokoi et al. | |
| 2003/0195415 A1 | 10/2003 | Iddan | |
| 2003/0208107 A1 | 11/2003 | Rafel | |
| 2003/0216622 A1 | 11/2003 | Meron et al. | |
| 2004/0027459 A1 | 2/2004 | Segawa et al. | |
| 2004/0027500 A1 | 2/2004 | Davidson et al. | |
| 2004/0087832 A1 | 5/2004 | Glukhovsky et al. | |
| 2004/0106849 A1 * | 6/2004 | Cho et al. | 600/101 |
| 2004/0171914 A1 * | 9/2004 | Avni | 600/160 |
| 2004/0215059 A1 * | 10/2004 | Homan et al. | 600/160 |
| 2004/0225189 A1 * | 11/2004 | Kimoto et al. | 600/160 |
| 2004/0225190 A1 * | 11/2004 | Kimoto et al. | 600/177 |
| 2004/0254455 A1 | 12/2004 | Iddan | |
| 2004/0258328 A1 | 12/2004 | Adler | |
| 2005/0025368 A1 | 2/2005 | Glukhovsky | |
| 2005/0043586 A1 * | 2/2005 | Suzushima | 600/160 |
| 2005/0049461 A1 * | 3/2005 | Honda et al. | 600/160 |
| 2005/0068416 A1 * | 3/2005 | Glukhovsky et al. | 348/77 |
| 2005/0259487 A1 | 11/2005 | Glukhovsky et al. | |
| 2006/0004257 A1 | 1/2006 | Gilad et al. | |
| 2006/0155174 A1 | 7/2006 | Glukhovsky et al. | |
| 2006/0241422 A1 | 10/2006 | Muratayev et al. | |

FOREIGN PATENT DOCUMENTS

| | | |
|---|---|---|
| FR | 2362556 | 3/1978 |
| FR | 2 688 997 | 3/1992 |
| GB | 2 291 980 | 2/1996 |
| IL | 143259 | 11/2006 |
| JP | 57-45833 | 3/1982 |
| JP | 01-111399 | 4/1989 |
| JP | HEI 3-289779 | 12/1991 |
| JP | HEI 4-109927 | 4/1992 |
| JP | 1992-144533 | 5/1992 |
| JP | 4144533 | 5/1992 |
| JP | HEI 4-180736 | 6/1992 |
| JP | 04-319337 | 11/1992 |
| JP | 5015515 | 1/1993 |
| JP | 6114037 | 4/1994 |
| JP | 6285044 | 10/1994 |
| JP | 7111985 | 5/1995 |
| JP | 7289504 | 11/1995 |
| JP | 9238900 | 9/1997 |
| JP | 2000-342522 | 12/2000 |
| JP | 2000-342524 | 12/2000 |
| JP | 2000-342526 | 12/2000 |
| JP | 2001-094252 | 4/2001 |
| JP | 2001-112709 | 4/2001 |
| JP | 2001-112710 | 4/2001 |
| JP | 2001-112740 | 4/2001 |
| JP | 2001091860 | 4/2001 |
| JP | 2001095755 | 4/2001 |
| JP | 2001104241 | 4/2001 |
| JP | 2001104242 | 4/2001 |
| JP | 2001104243 | 4/2001 |
| JP | 2001104244 | 4/2001 |
| JP | 2001104287 | 4/2001 |
| JP | 2001-137182 | 5/2001 |
| JP | 2001137182 | 5/2001 |
| JP | 2001 224551 | 8/2001 |
| JP | 2001-231744 | 8/2001 |
| JP | 2001224553 | 8/2001 |
| JP | 2001-245844 | 9/2001 |
| JP | 2001 95756 | 10/2001 |
| WO | WO 92/21307 | 12/1992 |
| WO | WO 98/11816 | 3/1998 |
| WO | WO 00/22975 | 4/2000 |
| WO | WO 00/69324 | 11/2000 |
| WO | WO 01/08548 | 2/2001 |
| WO | WO 01/50941 | 7/2001 |
| WO | WO 01/65995 | 9/2001 |
| WO | WO 01/69212 | 9/2001 |
| WO | WO 02/055126 | 7/2002 |
| WO | WO 02/067593 | 8/2002 |
| WO | WO 02/094337 | 11/2002 |
| WO | WO 02/095351 | 11/2002 |
| WO | WO 02/102224 | 12/2002 |
| WO | WO 03/003706 | 1/2003 |
| WO | WO 03/011103 | 2/2003 |

| WO | WO 2004/028335 | 4/2004 |
| WO | WO 2004/028336 | 4/2004 |
| WO | WO 2004-028336 | 4/2004 |
| WO | WO 2004/035106 | 4/2004 |
| WO | WO 2004/088448 | 10/2004 |
| WO | WO 2006-070360 | 7/2006 |

OTHER PUBLICATIONS

Robots for the future—Shin-ichi, et al., Nov. 29, 2001.
The Radio Pill, Rowlands, et al., British Communications and Electronics, Aug. 1960, pp. 598-601.
Video Camera to "TAKE"—RF System lab, Dec. 25, 2001.
Wellesley company sends body montiors into space—Crum, Apr. 1998.
www.rfnorkia.com—NORIKA3, Dec. 24, 2001.
Wireless transmission of a color television moving image from the stomach using a miniature CCD camera, light source and microwave transmitter. Swain CP, Gong F, Mills TN. Gastrointest Endosc 1997;45:AB40.
BBC News Online—Pill camera to 'broadcast from the gut', Feb. 21, 2000, www.news.bbc.co.uk.
Wang, et al., "Integrated Micro-Instrumentation for Dynamic Monitoring of the Gastro-Intestinal Tract", Presented at IEEE Instrumentation and Measurement Technology Conference, May 2002, Anchorage, Ak, USA, www.see.ed.ac.uk/Naa.publications.html.
International Search Report for PCT/IL02/00480 dated Sep. 17, 2003.
Gavriel D. Meron: "The Development of the Swallowable Video Capsule (M2A)" Gastrointestinal Endoscopy , vol. 52, No. 6, Dec. 2000, pp. 817-819.
Appleyard et al. "A Randomized Trial Comparing Wireless Capsule Endoscopy With Push Enteroscopy for the Detection of Small-Bowel Lesions" Gastroenterology, vol. 119, No. 6, Dec. 2000, pp. 1431-1438.
European Search Report for Application No. 02 738602.8 Completed Feb. 16, 2005.
European Office Action for Application No. 02 738602.8 Dated Dec. 12, 2006.
Office Action for U.S. Appl. No. 10/481,126 mailed Feb. 24, 2006.
Office Action for U.S. Appl. No. 10/481,126 mailed Oct. 10, 2006.
Office Action for U.S. Appl. No. 10/481,126 mailed Mar. 29, 2007.
International Search Report for PCT/IL05/01380 mailed May 19, 2006.
U.S. Appl. No. 10/166,025, filed Jun. 11, 2002, Lewkowicz et al.
U.S. Appl. No. 10/213,345, filed Aug. 7, 2002, Glukhovsky et al.
Lange et al., Heidelberger Kapsel-ein Kleinstsender fur die Ph-Messung im Magen, Telefunken-Zeitung, Jg 36 (1963) Heft 5, pp. 265-270.
Turke, "New Smart Plastic has Good Memory", European Medical Device Manufacturer, devicelink.com, Sep. 2001.
Craford et al., In Pursuit of the Ultimate Lamp, Scientific American, Feb. 2001.
Manual of Photogrammetry, Thompson (Ed.), Third Edition, Volume Two, American Society of Photogrammetry (1966).
www.jason.net—Tiny cam © 2000.
www.middleeasthealthmag.com—Review proves the value of computers, dated Nov. 29, 2001.
www.pedinc.com—Personal electronic devices © 1997.
The Heidelburg Ph Capsule System Telemetric Fasting Gastric Analysis, date unknown.
Final Office Action for U.S. Appl. No. 10/481,126 mailed on Aug. 4, 2009.
Action for U.S. Appl. No. 11/268,463 mailed on Mar. 19, 2009.
Office Action for U.S. Appl. No. 11/280,468 mailed on Dec. 16, 2009.

* cited by examiner

IN VIVO DEVICE WITH FLEXIBLE CIRCUIT BOARD AND METHOD FOR ASSEMBLY THEREOF

FIELD OF THE INVENTION

The present invention relates to an in vivo device, such as an imaging device, and a method for manufacture thereof.

BACKGROUND OF THE INVENTION

Devices helpful in providing in-vivo imaging are known in the field. Autonomous in-vivo imaging devices, such as swallowable or ingestible capsules or other devices may move through a body lumen, imaging as they move along. In vivo imaging may require in-vivo illumination, for example, using one or more LEDs or other suitable sources positioned inside an in-vivo imaging device.

In some ingestible devices the electronic components within the device may be arranged on several boards, each board containing different components of the device. The image sensor, for example a silicon chip, may be positioned on one board whereas a transmitter for transmitting images may be positioned on a separate printed circuit board (PCB).

In some cases the different components must be aligned so that certain parts are positioned at specific angles for optimal operation to be achieved.

In some cases the boards are arranged along an axis of the device and are electrically connected by one or more wires. The assembly of devices having several boards connected by wires may be complex and may hinder, for example, large scale production.

SUMMARY OF THE INVENTION

Thus the present invention provides, according to some embodiments, an in vivo device such as an imaging device including a one sheet circuit board According to one embodiment the circuit board may include at least one leaf (for example, a tongue-shaped component). Other numbers of sheets or leaves may be used. According to an embodiment of the invention a unique shape and various folding options of the leaves may enable folding and positioning of components attached to the flexible circuit board according to, for example, a predefined angle.

Optionally, the in vivo imaging device may include at least an image sensor and an illumination source. According to another embodiment the device may also include a transmitter for transmitting signals from a sensor, such as an image sensor, to a receiving system. In one embodiment various components in the device, such as the image sensor and illumination source, may be disposed on different flexible circuit board sections, for example, on the flexible leaves.

According to an embodiment, the circuit board may be folded and arranged in a stacked vertical fashion.

Additionally, upon folding and inserting the flexible circuit board into the device the leaves may be folded in an angle required for the illumination sources mounted on the leaves to provide illumination as needed. For example, a number of illumination sources mounted on the leaves may fold such that outwards panoramic illumination is achieved.

In another embodiment different components of the system may be mounted on the circuit board and may be folded as necessary.

In another embodiment the circuit board may be capable of folding according to several designs, enabling the circuit board to fit into devices of different shapes and/or sizes.

Additionally, the device and method of some embodiments of the present invention may enable easy access to key components of the device even after their assembly and incorporation into the system.

Additionally, the device and method of some embodiments of the present invention may enable exact and meticulous assembly, finish and performance while keeping maintenance and costs of the parts at a minimum.

Additionally, embodiments of the present invention may enable assembly of parts to create a variety of shapes.

Additionally, the device according to embodiments of the present invention may be lightweight and flexible, enabling quick transformation and adjustment of shape and function according to the specific needs and requirement of the procedure performed.

BRIEF DESCRIPTION OF THE DRAWINGS

The principles and operation of the system, apparatus, and method according to the present invention may be better understood with reference to the drawings, and the following description, it being understood that these drawings are given for illustrative purposes only and are not meant to be limiting, wherein.

Figure 1:
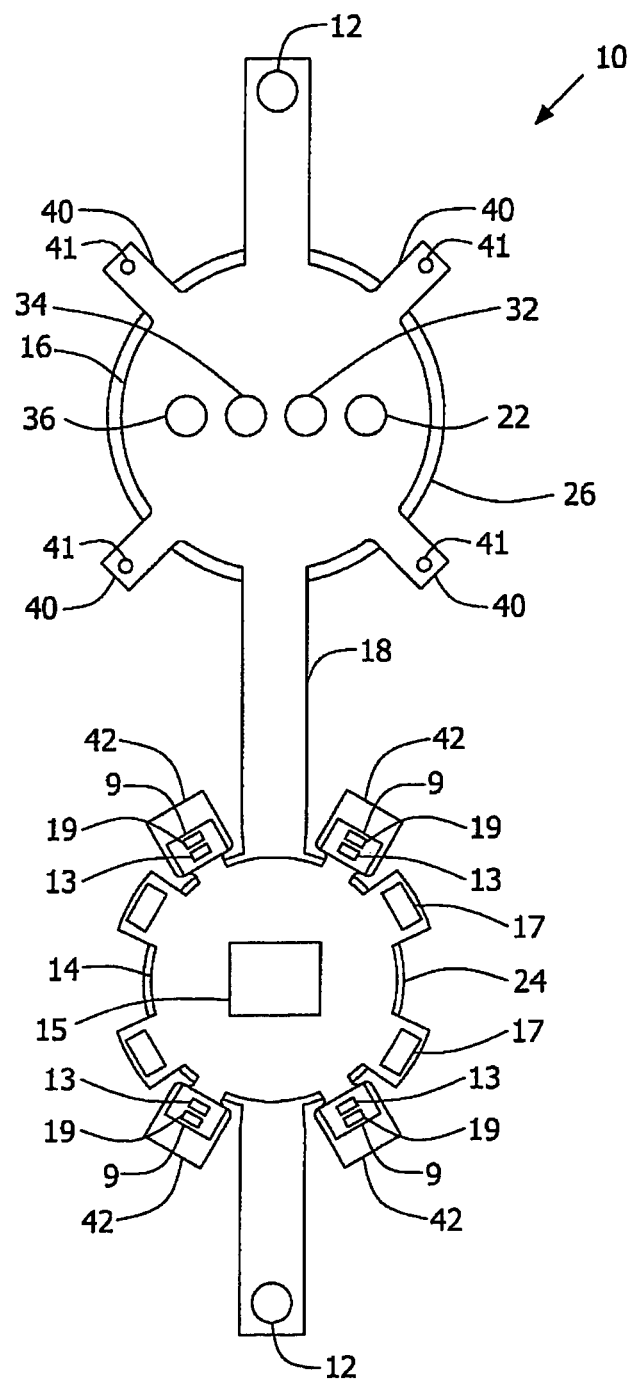
FIG. 1 is a schematic illustration showing an exemplary embodiment of a one sheet flexible circuit board in its spread out form, before it is folded and inserted into a device, according to one embodiment of the invention.

It should be noted that for simplicity and clarity of illustration, elements shown in the figures have not necessarily been drawn to scale. For example, the dimensions of some of the elements may be exaggerated relative to other elements for clarity. Furthermore, where considered appropriate, reference numerals may be repeated among the figures to indicate corresponding or analogous elements throughout the serial views.

DETAILED DESCRIPTION OF THE INVENTION

The following description is presented to enable one of ordinary skill in the art to make and use the invention as provided in the context of a particular application and its requirements. Various modifications to the described embodiments will be apparent to those with skill in the art, and the general principles defined herein may be applied to other embodiments. Therefore, the present invention is not intended to be limited to the particular embodiments shown and described, but is to be accorded the widest scope consistent with the principles and novel features herein disclosed. In the following detailed description, numerous specific details are set forth in order to provide a thorough understanding of the present invention. However, it will be understood by those skilled in the art that the present invention may be practiced without these specific details. In other instances, well-known methods, procedures, and components have not been described in detail so as not to obscure the present invention.

Illumination sources used with embodiments of the present invention may include, for example, Light Emitting Diodes (LEDs), incandescent sources, or other suitable light sources that may enable in-vivo illumination, and may encompass devices providing electromagnetic radiation within the visible spectrum, outside of the visible spectrum, and further a combination of visible and non-visible electromagnetic radiation.

Some embodiments of the present invention are directed to a typically swallowable in-vivo device that may be used for recording and transmitting in vivo data, such as, for example, from the entire length of the gastrointestinal (GI) tract, to a receiving and/or processing unit. Other embodiments need not be swallowable or autonomous, and may have other shapes or configurations. According to some embodiments the in vivo device may include an image sensor, however, other sensors may be used. Devices according to embodiments of the present invention may be similar to embodiments described in International Application WO 01/65995 and/or in U.S. Pat. No. 5,604,531, each of which are assigned to the common assignee of the present invention and each of which are hereby incorporated by reference in their entirety. Furthermore, receiving, storage, processing and/or display systems suitable for use with embodiments of the present invention may be similar to embodiments described in WO 01/65995 and/or in U.S. Pat. No. 5,604,531. Of course, devices, systems, structures, functionalities and methods as described herein may have other configurations, sets of components and processes etc.

Reference is now made to FIG. 1 showing an exemplary embodiment of a one sheet flexible circuit board 10 in its spread out form, before it is folded and inserted into an in-vivo device, for example, a capsule, according to an embodiment of the invention. Devices having forms other than capsules may be used. According to some embodiments the flexible circuit board 10 may be a printed circuit board (PCB) made of, for example, silicone or plastic. Other suitable materials may be used. In one embodiment of the invention flexible circuit board 10 may include one or more battery contacts 12, for example, placed at each end, and one or more (e.g., two) wider portions 14 and 16, connected to one another by means of a narrowed flexible circuit board strip 18. Underneath each flexible portion 14 and 16, a rigid portion 24 and 26 may be attached, respectively, enabling, for example, the stability of the components each portion holds. According to one embodiment a portion or section of the circuit board may have a set of components mounted or disposed upon it. According to one embodiment portion 16 of the circuit board, for example, may include components such as a switch 34, a transmitter, processor or controller such as an ASIC (Application Specific Integrated Circuit) 36, a silicon timer 22 and an antenna 32, while the other portion 14 of the circuit board 10 may have an imaging system 11, for example, for obtaining images from inside a body lumen, mounted upon it. Other components and sets of components may be used. The imaging system may include one or more illumination units 9, an image sensor such as an imaging camera 15 and for example one or more capacitors 17. The illumination unit 9 may include one or more illumination sources 13, such as white LEDs, and one or more resistors 19. According to one embodiment the circuit board components may be arranged on one side of the circuit board 10, enabling comfortable accessibility during a device production process. In alternate embodiments, other components layouts may be arranged on a flexible circuit board with a different shape.

According to one embodiment of the present invention, as seen, for example, with reference to FIG. 1, flexible leaves 42 and 40 may be formed, respectively, of the circuit board portions 14 and 16, including different components. According to one embodiment flexible leaves 40 protruding from flexible portion 16 may comprise for example test points 41, while flexible leaves 42 protruding from flexible circuit board 14 may include one or more illumination units 9. Each illumination unit 9 may comprise, for example, at least one illumination source 13 and resistors 19. Flexible leaves 42 protruding from portion 14 may be folded inwards at a required angle when the flexible circuit board 10 is inserted into a housing tube, for example a capsule housing tube (as will be described, for example, with reference to FIG. 2). The shape and proportions of the device housing may determine the exact angle in which each flexible leave 42 will fold upon insertion of the circuit board. According to one embodiment the angles thus created, enable the illumination units 13, mounted on the leaves 42, to create the specific field and angle of illumination required.

In addition, flexible leaves 40 protruding from portion 16 may also be folded inwards at a required angle when the flexible circuit board is inserted into a housing tube.

According to one embodiment, a flexible circuit board 10 length in its spread out form may be equal to or less than about 36.5 mm (measured between the centers of battery contacts 12) while its breadth may be less or more than about 13 mm (measured between the edges of flexible portions 14 and 16). Such a flexible circuit board may be suitable for use in a device that is about 20-30 mm long. Flexible circuit boards and micro technology according to embodiments of the invention may be similar to flexible boards produced by Altech of Petach-Tikva, Israel. Other dimensions or sizes may be used.

Figure 2:
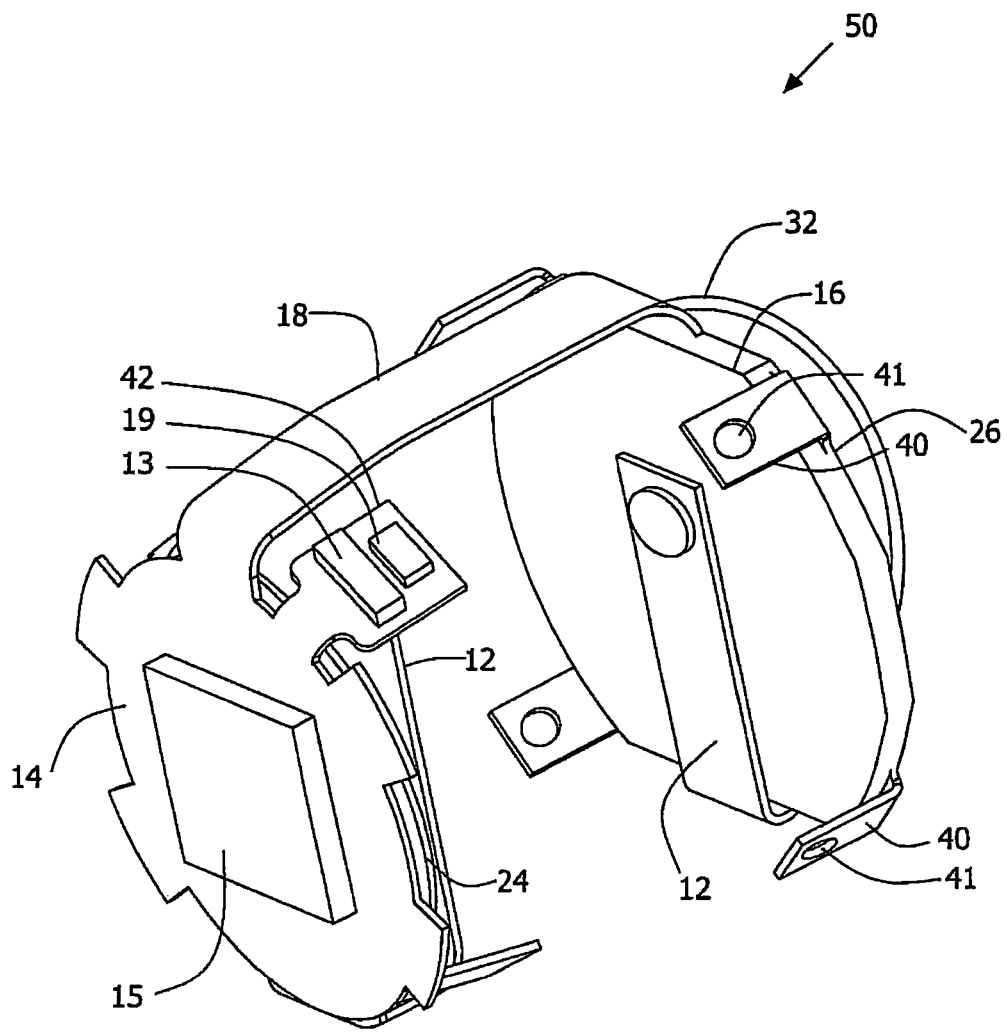
FIG. 2 schematically illustrates possible folding of the flexible circuit board according to one embodiment of the invention.

Reference is now made to FIG. 2 showing an exemplary embodiment of a flexible circuit board 50 shape after it has been folded and inserted into an in vivo device, for example, a capsule. While the invention is shown in use with a capsule, other in-vivo devices may house embodiments of the invention, and devices may be used having other configurations (e.g., spherical, rounded, an endoscope, etc.). According to one embodiment of the present invention, flexible circuit board portions 14 and 16 may be folded upon insertion so that they are facing each other resulting in for example a "C" shape. In this folded state, according to one embodiment, antenna 32 and an imaging device such as imaging camera 15 are facing outwards while battery contacts 12 are folded under flexible portions 14 and 16 which may, according to some embodiments, having rigid portions 24 and 26 attached to them, for example, so that contact may be made with a set of batteries which may be sandwiched between circuit board portions 16 and 14. According to one embodiment, flexible leaves 42 holding illumination sources 13 and resistors 19 may, for example bend in a range of degrees upon inserting the flexible circuit board into a device housing tube so as to enable, for example, an outwards illumination at different angles. The illumination angle may be determined by for example the housing tube shape. In another embodiment of the present invention, test points 41 placed on flexible leaves 40, may be folded inwards so as to allow a better space utilization in a device. In some embodiments of the present invention, various components may be sandwiched between or otherwise disposed between circuit board portions.

The folding of the leaves 40 upon which the test points 41 are mounted may enable preservation of the test points without wasting any valuable space. This method of preserving the test points instead of cutting and removing them, prior to packaging the circuit board into a device, may save time and may reduce the risk of short circuiting the system as is often the case in systems where the test points need to be cut off and removed prior to use. According to an embodiment the flexible circuit board 50 offers little manufacturing and assembly hindrances such as delicate and expensive welding of parts, sophisticated manufacturing protocols etc.

Different arrangements may determine the exact folding of the flexible circuit board and components, enabling different angles and scopes of, for example, illumination and camera rotation. Different folding options of the flexible circuit board may free up more space in accordance with the number of mounted and loose components that need to be housed within a device shell.

Figure 3:
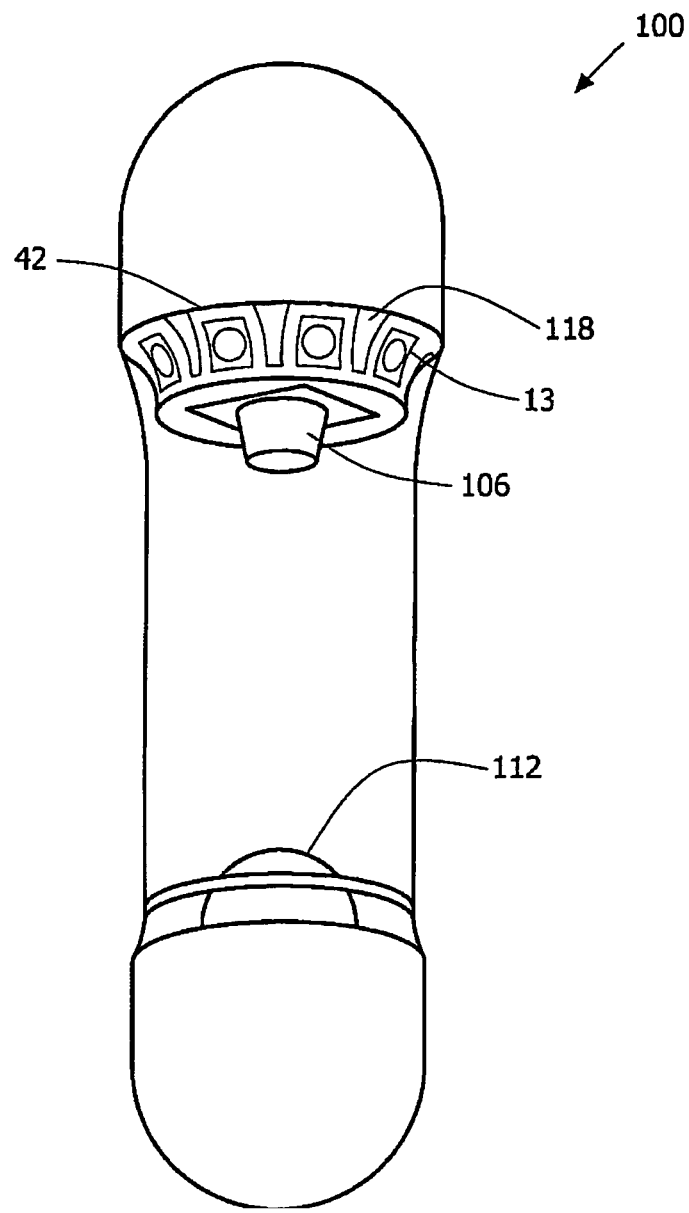
FIG. 3 shows a schematic illustration of an in-vivo imaging device according to one embodiment of the invention.

In one embodiment the flexible circuit board may be incorporated into a device such as a panoramic field of view imaging device, for example, as shown schematically in FIG. 3. Other suitable imaging or sensing devices, including or not including panoramic viewing, may be used with embodiments of the present invention. Device 100 may include for example a transmitter, a processor, a receiver, an Image sensor 106, a power supply, one or more illuminators 13 and a reflective element such as for example a mirror or a curved mirror 112. According to some embodiments, other sensors except an image sensor may be used e.g., a temperature sensor, a pH sensor, a pressure sensor, an electrical impedance sensor, sensors of physiological parameters of the body lumen, etc.

According to one embodiment, for example as shown in FIG. 3, illumination sources 13 may be on flexible circuit board leaves 42 slanted outward in relation to the plane of an image sensor 106.

In one embodiment the flexible circuit board leaves 42 are part of a flexible circuit board 10. In another embodiment, some components need not be situated on the flexible circuit board, for example illumination sources 13 may be situated, for example, on an outward facing ring 118 such that illuminators face outward and away from image sensor.

Figure 4:
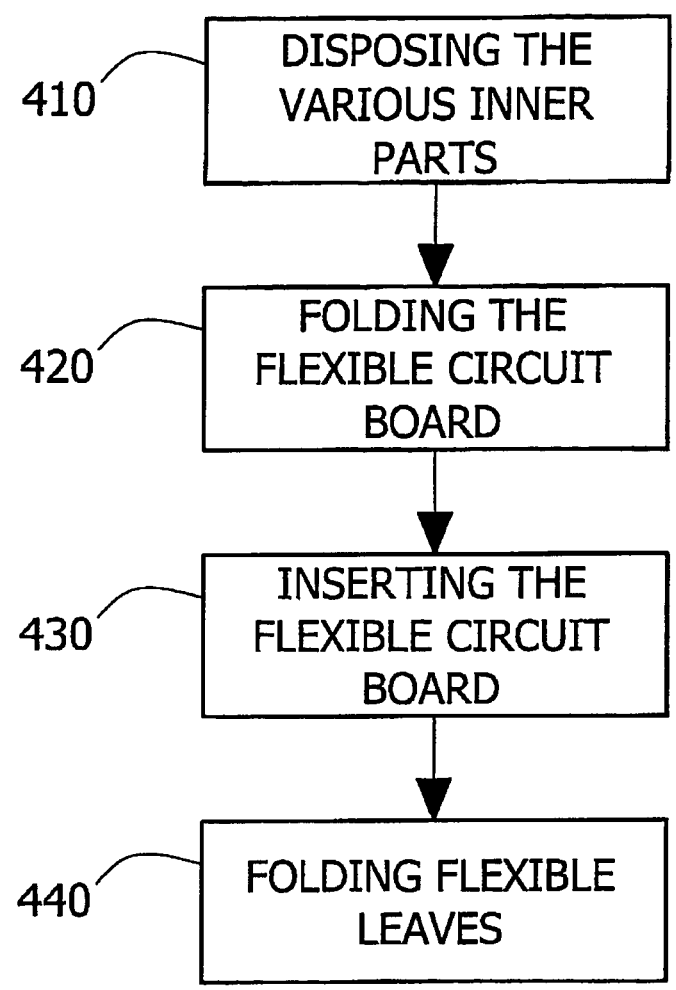
FIG. 4 is a flowchart depicting a method for producing an in vivo device which includes a flexible circuit board, according to embodiments of the invention.

A method for producing an in vivo imaging device which includes a flexible circuit board 10, according to different embodiments of the invention is depicted in FIG. 4.

Step 410 according to some embodiments includes placing various inner parts of the device on a flexible circuit board (e.g., board 10). For example, a switch 34, an ASIC (Application Specific Integrated Circuit) 36 and a silicon timer 22 may be disposes on flexible section 16 (as was described with reference to FIG. 1). Other specific components may be Used. Step 420 includes, for example, folding portions of the flexible circuit board (e.g., portions 14 and 16) so that they are "C" shaped, facing each other (as was described with reference to FIG. 2). Other suitable configurations and folding arrangements can be used.

According to one embodiment of the present invention, in step 430 the flexible circuit board, may be inserted into a housing, for example a device housing tube. According to one embodiment, in step 440 flexible leaves which may be protruding from portions 14 and 16 may be folded inwards at a required angle when the flexible circuit board is inserted into a housing tube.

The foregoing description of the embodiments of the invention has been presented for the purposes of illustration and description. It is not intended to be exhaustive or to limit the invention to the precise form disclosed. It should be appreciated by persons skilled in the art that many modifications, variations, substitutions, changes, and equivalents are possible in light of the above teaching. It is, therefore, to be understood that the appended claims are intended to cover all such modifications and changes as fall within the true spirit of the invention.

What is claimed is:

1. An autonomous in vivo imaging device comprising:
    a device housing; and
    a flexible circuit board inserted within said housing, the flexible circuit board comprising:
        a first portion having components mounted thereon, said first portion defining a plane, and
        a plurality of flexible leaves extending from the perimeter of said first portion, said flexible leaves abutting against said housing and being disposed at an angle with respect to the plane of the first portion, said angle being determined by the inner wall of said housing when said leaves abut said housing,
        wherein at least one of said plurality of flexible leaves comprises an illumination source mounted thereon such that the illumination source abuts said housing;
        wherein said plurality of flexible leaves comprises at least four flexible leaves, each protruding outwardly from the perimeter of said first portion in a respective plurality of radial directions.

2. The device according to claim 1, wherein said plurality of flexible leaves are for being folded at a required angle in relation to an axis of said in vivo device.

3. The device according to claim 2, wherein said angle is determined by the shape of the device housing.

4. The device according to claim 1, wherein said circuit board is a PCB.

5. The device according to claim 1, further comprising a sensor.

6. The device according to claim 5, wherein said sensor is an image sensor.

7. The device according to claim 5, wherein the sensor is selected from the group consisting of a pH sensor, a temperature sensor, an electrical impedance sensor and a pressure sensor.

8. The device according to claim 1, wherein a sensor is disposed on said first portion of said circuit board and a transmitter is disposed on a second portion of said circuit board.

9. The device according to claim 1, wherein said illumination source illuminates in a direction towards a side of said housing.

10. The device according to claim 1, wherein each of said plurality of flexible leaves is folded at a different angle in relation to a longitudinal axis of said in vivo device.

11. An autonomous in vivo imaging device comprising:
    a device housing; and
    a flexible circuit board inserted within said housing, the flexible circuit board comprising:
        a first portion having components mounted thereon, said first portion defining a plane, and
        a plurality of flexible leaves extending from the perimeter of said first portion, said flexible leaves abutting against said housing and being disposed at an angle with respect to the plane of the first portion, said angle being determined by the inner wall of said housing when said leaves abut said housing,
        wherein each of said plurality of flexible leaves comprises an illumination source mounted thereon such that said illumination sources abut said housing and illuminate at different angles in relation to a longitudinal axis of said in vivo device.

12. The device according to claim 11, wherein said plurality of flexible leaves are for being folded at a required angle in relation to an axis of said in vivo device.

13. The device according to claim 12, wherein said angle is determined by the shape of the device housing.

14. The device according to claim 11, wherein said circuit board is a PCB.

15. The device according to claim 11, further comprising a sensor.

16. The device according to claim 15, wherein said sensor is an image sensor.

17. The device according to claim 15, wherein the sensor is selected from the group consisting of a pH sensor, a temperature sensor, an electrical impedance sensor and a pressure sensor.

18. The device according to claim 11, wherein a sensor is disposed on said first portion of said circuit board and a transmitter is disposed on a second portion of said circuit board.

19. The device according to claim 16 wherein the imager is positioned on the first portion.

20. The device according to claim 11, wherein each of said illumination sources illuminate in a direction towards a respective side of said housing.

* * * * *